US009642357B2

(12) United States Patent
Sano et al.

(10) Patent No.: US 9,642,357 B2
(45) Date of Patent: May 9, 2017

(54) OIL-BASED PESTICIDAL SUSPENSION

(71) Applicant: ISHIHARA SANGYO KAISHA, LTD., Osaka (JP)

(72) Inventors: Mitsuo Sano, Shiga (JP); Takashi Okada, Shiga (JP); Yasuhiro Okumura, Shiga (JP); Mitsugu Iwasa, Shiga (JP); Yusuke Kobayashi, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 14/647,621

(22) PCT Filed: Dec. 5, 2013

(86) PCT No.: PCT/JP2013/083276
§ 371 (c)(1),
(2) Date: May 27, 2015

(87) PCT Pub. No.: WO2014/088121
PCT Pub. Date: Jun. 12, 2014

(65) Prior Publication Data
US 2015/0296771 A1 Oct. 22, 2015

(30) Foreign Application Priority Data

Dec. 6, 2012 (JP) .................. 2012-267685

(51) Int. Cl.
| A01N 25/02 | (2006.01) |
| A01N 43/40 | (2006.01) |
| A01N 25/30 | (2006.01) |

(52) U.S. Cl.
CPC ............. *A01N 25/02* (2013.01); *A01N 25/30* (2013.01); *A01N 43/40* (2013.01)

(58) Field of Classification Search
None
See application file for complete search history.

(56) References Cited

U.S. PATENT DOCUMENTS

| 4,028,218 A | 6/1977 | Fink et al. |
| 6,375,965 B1 | 4/2002 | Matsuo et al. |
| 8,709,513 B2 * | 4/2014 | Gutsche ................. A01N 41/02 424/757 |
| 9,332,756 B2 * | 5/2016 | Gutsche ................. A01N 43/56 |
| 2002/0142021 A1 | 10/2002 | Matsuo et al. |
| 2005/0255171 A1 | 11/2005 | Matsuo et al. |
| 2011/0028521 A1 | 2/2011 | Morita et al. |

FOREIGN PATENT DOCUMENTS

| CN | 1465247 | 1/2004 |
| CN | 101785455 | 7/2010 |
| EP | 2263455 | * 12/2010 |
| JP | 51-10188 | 1/1976 |
| WO | 89/12393 | 12/1989 |
| WO | 90/03111 | 4/1990 |
| WO | 94/00010 | 1/1994 |
| WO | 98/48628 | 11/1998 |
| WO | 99/53764 | 10/1999 |
| WO | 2013/054194 | 4/2013 |

OTHER PUBLICATIONS

Opposition in Costa Rican Office Action with English Translation in respect to Costa Rican Application No. 2015-0270, dated Oct. 1, 2015.
Moroccan Office Action with English Translation in respect to Moroccan Application No. 37148, dated Feb. 8, 2016.
International Search Report in respect to PCT/JP2013/083276, dated Feb. 10, 2014.
Written Opinion of the International Searching Authority for PCT/JP2013/083276, dated Feb. 10, 2014.
Taiwanese Office Action and attached Search Report with English Translation in respect to Taiwanese Application No. 102142694, dated Oct. 25, 2016.
"Preparation and application of polyether type organosiloxane surfactants", Silicone and Fluorine Information, vol. 3-4, 2005, pp. 11-14 and 43.
Chinese Office Action with English Translation in respect to Chinese Application No. 201380063479, dated Aug. 26, 2016.
Fei Youchun, "A Concise Dictionary of Pesticides", Chemical Industry Press, pp. 67-68.
Guo Wudi, "Liquid Preparations $3^{rd}$ Edition", Chemical Industry Press, Jan. 31, 2004, pp. 246-248.
Chinese Office Action with English Translation in respect to Chinese Application No. 201380063479, dated Feb. 1, 2016.
Fu Yang et al. "Preparation and Application of Polyether Organic Silicone Type Surfactant", Silicone and Fluorine Information, issues 3-4, pp. 11-14 and 43, 20050425.
Japanese Office Action with English Translation in respect to Japanese Application No. 2013-237456, dated Mar. 6, 2017.

* cited by examiner

*Primary Examiner* — Karl J Puttlitz
(74) *Attorney, Agent, or Firm* — Greenblum & Bernstein, P.L.C.

(57) ABSTRACT

To provide an oil-based pesticidal suspension which suppresses foaming at the time of preparation of a spray liquid by an organic silicone type surfactant, and which has excellent pesticidal activity with a small amount of an agricultural chemical.
The present invention provides an oil-based pesticidal suspension comprising (1) flonicamid or its salt, (2) an organic silicone type surfactant and (3) at least one oil-based diluting agent selected from the group consisting of a vegetable oil and its alkylated oil, and a method for controlling pests, which comprises applying the oil-based pesticidal suspension to the pests or to a place where they grow.

12 Claims, No Drawings

OIL-BASED PESTICIDAL SUSPENSION

TECHNICAL FIELD

The present invention relates to an oil-based pesticidal suspension comprising flonicamid or its salt as an active ingredient, containing an organic silicone type surfactant.

BACKGROUND ART

In recent years, in view of reduction of the environmental burden, various attempts have been carried out to securely achieve pesticidal effects while the amount or the number of agricultural chemicals used is reduced. One method is to enhance the effects by addition of adjuvants.

As adjuvants, usually, a nonionic surfactant such as a polyoxyethylene alkylphenyl ether, a polyoxyethylene alkyl ether or a polyoxyethylene higher fatty acid ester, or an organic silicone type surfactant is used, and particularly an organic silicone type surfactant is known to have excellent effects by virtue of its low toxicity and high surfactant potency. However, a diluted solution (spray solution) of an agricultural chemical having such a spreader added has a lowered surface tension and is thereby likely to foam, such being problematic when used. Accordingly, an antifoaming agent is added for the purpose of preventing foaming when an aqueous dispersion of an agricultural chemical is prepared, however, it is very difficult to completely suppress foaming even by addition of an antifoaming agent since an organic silicone type surfactant has high surfactant potency.

PRIOR ART DOCUMENT

Patent Document

Patent Document 1: European Patent Publication No. 2,263,455

DISCLOSURE OF INVENTION

Technical Problem

Patent Document 1 discloses a pesticidal composition comprising a specific pyridine compound or its salt, and at least one potency-enhancing component selected from the group consisting of a silicone type surfactant, a nonionic surfactant, an anionic surfactant, a cationic surfactant, an amphoteric surfactant, an animal or plant oil, a mineral oil, a water-soluble polymer, a resin and a wax. However, if a highly formable silicone type compound is selected as the potency-enhancing agent, although the effects are sufficiently enhanced, a large amount of foam will form at the time of preparation of a spray solution. Thus, suppression of foaming is a practically great object to be attained, and a pesticidal composition which sufficiently has both pesticidal effects and foaming-suppressing effects has been desired.

Solution to Problem

The present inventors have conducted extensive studies to achieve the above object and as a result, accomplished the present invention.

That is, the present invention provides an oil-based pesticidal suspension comprising (1) flonicamid or its salt, (2) an organic silicone type surfactant and (3) at least one oil-based diluting agent selected from the group consisting of a vegetable oil and its alkylated oil, and a method for controlling pests, which comprises applying the oil-based pesticidal suspension to the pests or to a place where they grow. The present invention further provides a method of suppressing foaming which occurs when an oil-based pesticidal suspension comprising (1) flonicamid or its salt, (2) an organic silicone type surfactant and (3) at least one oil-based diluting agent selected from the group consisting of a vegetable oil and its alkylated oil, is diluted with water, by the oil-based diluting agent (3), and use of the oil-based diluting agent (3) to suppress foaming which occurs when an oil-based pesticidal suspension comprising (1) flonicamid or its salt, (2) an organic silicone type surfactant and (3) at least one oil-based diluting agent selected from the group consisting of a vegetable oil or its alkylated oil, is diluted with water.

Advantageous Effects of Invention

An oil-based pesticidal suspension which is less likely to foam at the time of preparation of a spray solution, and which has excellent pesticidal activity with a small dose, is provided.

DESCRIPTION OF EMBODIMENTS

Flonicamid which is a pesticidally active ingredient is N-cyanomethyl-4-(trifluoromethyl)nicotinamide.

The organic silicone type surfactant mainly means a silicone oil having hydrophilicity imparted by introduction of organic functional groups such as polyether groups. In the organic silicone type surfactant, the organic groups to be introduced are various in addition to the polyether groups, and such organic silicone type surfactants may be used within the scope of the present invention. The organic silicone type surfactant having polyether groups introduced may, for example, be a compound represented by the following formula (I):

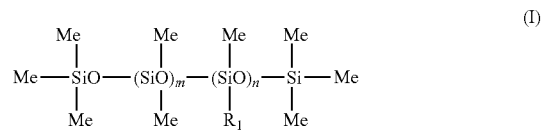

{wherein $R_1$ is an organic group represented by the following formula (II):

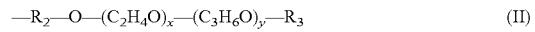

(wherein $R_2$ is a non-substituted or substituted $C_{2-6}$ alkylene group, $R_3$ is a hydroxy group, a non-substituted or substituted $C_{1-6}$ alkyl group or an acetyl group (—COCH$_3$), Me is a methyl group, x is an integer of from 0 to 15, and y is an integer of from 0 to 10), m is an integer of from 0 to 10, and n is an integer of from 1 to 10}.

Preferably, in the formula (I), $R_1$ is an organic group represented by the following formula (III):

(wherein $R_2$ is a propylene group, $R_3$ is a hydroxy group or a methyl group, and x is an integer of from 0 to 15), m is an integer of from 0 to 3, and n is 1.

The organic silicone type surfactant may, for example, be polyoxyethylene methyl polysiloxane, polyoxyalkylene methyl polysiloxane, trisiloxane ethoxylate or a polyether polymethyl siloxane copolymer. Among them, preferred is polyoxyethylene methyl polysiloxane, polyoxyalkylene methyl polysiloxane or trisiloxane ethoxylate, and more preferred is trisiloxane ethoxylate. However, the present invention is not limited thereto.

Further, as specific examples of the organic silicone type surfactant, the following (tradenames) may be mentioned. The polyoxyethylene methyl polysiloxane may, for example, be Makupika (manufactured by Ishihara Sankyo Kaisha, Ltd.). The polyoxyalkylene methyl polysiloxane may, for example, be KF-640 (manufatured by Shin-Etsu Chemical Co., Ltd.). The trisiloxane ethoxylate may, for example, be Silwet L-77, Silwet 408 or Silwet 440 (manufactured by Momentive Performance Materials Inc.) The polyether polymethyl siloxane copolymer may, for example, be Break-Thru (manufactured by Evonik Goldschmidt Chemical Corporation) or Break-Thru (manufactured by Sankei Chemical Co., Ltd.). Further, some commercially available silicone type surfactants further contain another component.

The oil-based diluting agent may be a vegetable oil or its alkylated oil, and is preferably an alkylated oil of a vegetable oil. However, the present invention is not limited thereto.

The vegetable oil may, for example, be olive oil, kapok oil, castor oil, papaya oil, camellia oil, coconut oil, sesame oil, corn oil, rice bran oil, peanut oil, cottonseed oil, soybean oil, rapeseed oil, linseed oil, tung oil, sunflower oil or safflower oil, and among them, preferred is olive oil, corn oil, soybean oil or rapeseed oil.

The alkylated oil (alkylated vegetable oil) may be a methylated or ethylated oil of the above vegetable oil, and is preferably a methylated oil. Among methylated oils, preferred is methylated soybean oil or methylated rapeseed oil, and more preferred is methylated rapeseed oil.

The above oil-based diluting agents may be used as a mixture of two or more if desired.

The oil-based pesticidal suspension of the present invention contains, when prepared into a formulation, (1) flonicamid or its salt, (2) an organic silicone type surfactant and (3) at least one oil-based diluting agent selected from the group consisting of a vegetable oil and its alkylated oil, and various adjuvants may be used if desired. The various adjuvants which can be used are not particularly limited so long as they are used in this technical field, and for example, an emulsifying agent, a solvent, an anti-settling agent, an antifoaming agent, an anti-freezing agent, an antioxidant, a gelling agent, a dispersion stabilizer, a phytotoxicity reducing agent, an anti-mold agent, a stabilizer and a preservative may, for example be mentioned. As specific examples of such various adjuvants, the following may be mentioned. Here, preparation into a formulation may be carried out in accordance with a common method in this technical field.

The emulsifying agent is not particularly limited so long as it is used in this technical field, and it may, for example, be an alkane sulfonate, a salt of α-sulfofatty acid, a dialkyl sulfosuccinate, an alkylaryl sulfonate, a salt of a condensate of naphthalene sulfonate with formalin, a polyoxyethylene alkyl ether, a polyoxyethylene alkylaryl ether, a polyoxyethylene styrylphenyl ether, a polyoxyethylene fatty acid ester, a polyoxyethylene sorbitan fatty acid ester, a polyoxyethylene sorbitol fatty acid ester, a polyoxyethylene castor oil, a polyoxyethylene hydrogenated castor oil, a polyglycerin fatty acid ester and a polyoxyethylene polyoxypropylene block copolymer. It is preferably a dialkyl sulfosuccinate, an alkylaryl sulfonate, a polyoxyethylene fatty acid ester, a polyoxyethylene sorbitol fatty acid ester, a polyoxyethylene castor oil or a polyoxyethylene hydrogenated castor oil, and they may be used as mixed as the case requires. It is more preferably an alkylaryl sulfonate, a polyoxyethylene sorbitol fatty acid ester, a polyoxyethylene castor or a mixture thereof, further preferably a polyoxyethylene sorbitol fatty acid ester. However, the present invention is not limited thereto.

The solvent may, for example, be an aliphatic hydrocarbon such as normal paraffin or isoparaffin, an aromatic hydrocarbon such as benzene, alkylbenzene, naphthalene, alkylnaphthalene, diphenyl or phenylxylylethane, a heterocyclic compound such as N-methylpyrrolidone or 1,3-dimethyl-2-imidazolidinone, an alcohol, an ether, a ketone or an ester, and they may be used as a mixture of two or more if desired.

The anti-settling agent may, for example, be silica, organic bentonite, bentonite, white carbon or aluminum magnesium silicate, and they may be used as a mixture of two or more if desired.

The antifoaming agent may, for example, be an alcohol such as isooctadecanol or methylated silicone, and they may be used as a mixture of two or more if desired.

The anti-freezing agent may, for example, be ethylene glycol, propylene glycol or glycerin, and they may be used as a mixture of two or more if desired.

The gelling agent may, for example, be silica, organic attapulgite, clay, hydrogenated castor oil, a higher fatty acid ester, a higher alcohol, a salt of a dialkyl sulfosuccinate, a salt of benzoic acid, an alkyl sulfate, a mixture of a polyacrylic acid polymer or a polyacrylic acid copolymer with water, or 12-hydroxystearic acid, and they may be used as a mixture of two or more if desired.

In the present invention, if desired, flonicamid or its salt may be mixed with or may be used in combination with other agricultural chemicals, such as an insecticide, a miticide, a nematicide, a soil insect pesticide, a fungicide, an antivirus agent, an attractant, a herbicide and a plant growth regulating agent, as the case requires, whereby more excellent effect and activity are obtained in some cases. For example, the range of pests to be controlled, the application time, the pesticidal activities, etc. may be improved to preferred directions. Flonicamid or its salt and such other agricultural chemicals may separately be formulated so that they may be mixed for use at the time of application, or they may be formulated together. The present invention includes such a mixed pesticidal composition, and a method for controlling pests using it.

As other agricultural chemicals which may be mixed with flonicamid or its salt, for example, the following compound groups may be mentioned. Even when not specifically mentioned, in a case where such compounds have salts, alkyl esters, structural isomers such as optical isomers, etc., they are, of course, all included.

The active ingredient compounds of the insecticide, the miticide, the nematicide or the soil insect pesticide, i.e. insecticidal compounds, in the above-mentioned other agricultural chemicals, include, for example (by common names, some of them are still in an application stage, or test codes of Japan Plant Protection Association):

organic phosphate compounds, such as profenofos, dichlorvos, fenamiphos, fenitrothion, EPN, diazinon, chlorpyrifos, chlorpyrifos-methyl, acephate, prothiofos, fosthiazate, cadusafos, disulfoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet, phorate, phoxim and triazophos;

carbamate compounds, such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC and fenothiocarb;

nereistoxin derivatives, such as cartap, thiocyclam, bensultap, thiosultap-sodium thiosultap-disodium, monosultap, bisultap and thiocyclam hydrogen oxalate;

organic chlorine compounds, such as dicofol, tetradifon, endosulfan, dienochlor and dieldrin;

organic metal compounds, such as fenbutatin oxide and cyhexatin;

pyrethroid compounds, such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, flumethrin and decamethrin;

benzoylurea compounds, such as diflubenzuron, chlorfluazuron, teflubenzuron, flufenoxuron, triflumuron, hexaflumuron, lufenuron, novaluron, noviflumuron, bistrifluron and fluazuron;

juvenile hormone-like compounds, such as methoprene, pyriproxyfen, fenoxycarb and diofenolan;

pyridazinone compounds, such as pridaben;

pyrazole compounds, such as fenpyroximate, fipronil, tebufenpyrad, ethiprole, tolfenpyrad, acetoprole, pyrafluprole and pyriprole;

neonicotinoids, such as imidacloprid, nitenpyram, acetamiprid, thiacloprid, thiamethoxam, clothianidin, nidinotefuran, dinotefuran and nithiazine;

hydrazine compounds, such as tebufenozide, methoxyfenozide, chromafenozide and halofenozide;

pyridine compounds, such as pyridalyl;

cyclic keto-enol compounds, such as spirodiclofen; spiromesifen and spirotetramat;

strobilurin compounds, such as fluacrypyrim;

pyrimidinamine compounds, such as flufenerim;

dinitro compounds; organic sulfur compounds; urea compounds; triazine compounds; hydrazone compounds;

other compounds, such as flometoquin, buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, propargite, clofentezine, metaflumizone, flubendiamide, cyflumetofen, chlorantraniliprole, cyantraniliprole, cyclaniliprole, cyenopyrafen, pyrifluquinazon, fenazaquin, amidoflumet, sulfluramid, hydramethylnon, metaldehyde, HGW-86, ryanodine, verbutin, AKD-1022, chlorobenzoate, thiazolylcinnanonitrile, sulfoxaflor, fluensulfone, triflumezopyrim, afidopyropen and flupyradifuron. Further, it may be used in combination with or together with microbial agricultural chemicals, such as insecticidal crystal proteins produced by *Bacillus thuringiensis* aizawai, *Bacillus thuringiensis* kurstaki, *Bacillus thuringiensis* israelensis, *Bacillus thuringiensis* japonensis, *Bacillus thuringiensis* tenebrionis or *Bacillus thuringiensis*, insect viruses, entomopathogenic fungi, and nematophagous fungi; antibiotics or semisynthetic antibiotics, such as avermectin, emamectin benzoate, milbemectin, milbemycin, spinosad, ivermectin, lepimectin, DE-175, abamectin, emamectin and spinetoram; natural products, such as azadirachtin and rotenone; and repellents, such as deet.

The active ingredient compounds of the fungicide, i.e. the fungicidal compounds, in the above-mentioned other agricultural chemicals include, for example (by common names, some of them are still in an application stage, or test codes of Japan Plant Protection Association):

anilinopyrimidine compounds, such as mepanipyrim, pyrimethanil, cyprodinil and ferimzone;

triazoropyrimidine compounds, such as 5-chloro-7-(4-methylpiperidin-1-yl)-6-(2,4,6-trifluorophenyl)[1,2,4]triazolo[1,5-a]pyrimidine;

pyridinamine compounds, such as fluazinam;

azole compounds, such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole and imibenconazole;

quinoxaline compounds, such as quinomethionate;

dithiocarbamate compounds, such as maneb, zineb, mancozeb, polycarbamate, metiram, propineb and thiram;

organic chlorine compounds, such as fthalide, chlorothalonil and quintozene;

imidazole compounds, such as benomyl, cyazofamid, thiophanate-methyl, carbendazim, thiabendazole and fuberiazole;

cyanoacetamide compounds, such as cymoxanil;

anilide compounds, such as metalaxyl, metalaxyl-M, mefenoxam, oxadixyl, ofurace, benalaxyl, benalaxyl-M (another name: kiralaxyl, chiralaxyl), furalaxyl, cyprofuram, carboxin, oxycarboxin, thifluzamide, boscalid, bixafen, isotianil, tiadinil and sedaxane;

sulfamide compounds, such as dichlofluanid;

copper compounds, such as cupric hydroxide and oxine copper;

isoxazole compounds, such as hymexazol;

organophosphorus compounds, such as fosetyl-Al, tolclofos-methyl, S-benzyl O,O-diisopropylphosphorothioate, O-ethyl S,S-diphenylphosphorodithioate, aluminum ethylhydrogen phosphonate, edifenphos, and iprobenfos;

phthalimide compounds, such as captan, captafol and folpet;

dicarboximide compounds, such as procymidone, iprodione and vinclozolin;

benzanilide compounds, such as flutolanil and mepronil;

amide compounds, such as penthiopyrad, mixture of 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide (isopyrazam), silthiopham, fenoxanil and furametpyr;

benzamide compounds, such as fluopyram and zoxamide;

piperazine compounds, such as triforine;

pyridine compounds, such as pyrifenox;

carbinol compounds, such as fenarimol;

piperidine compounds, such as fenpropidin;

morpholine compounds, such as fenpropimorph and tridemorph;

organotin compounds, such as fentin hydroxide and fentin acetate;

urea compounds, such as pencycuron;

cinnamic acid compounds, such as dimethomorph and flumorph;

phenylcarbamate compounds, such as diethofencarb;

cyanopyrrole compounds, such as fludioxonil and fenpiclonil;

strobilurin compounds, such as azoxystrobin, kresoxim-methyl, metominostrobin, trifloxystrobin, picoxystrobin, oryzastrobin, dimoxystrobin, pyraclostrobin, and fluoxastrobin;

oxazolidinone compounds, such as famoxadone;

thiazolecarboxamide compounds, such as ethaboxam;

valinamide compounds, such as iprovalicarb and benthiavalicarb-isopropyl;

acylamino acid compounds, such as methyl N-(isopropoxycarbonyl)-L-valyl-(3RS)-3-(4-chlorophenyl)β-alaninate (valiphenalate);

imidazolinone compounds, such as fenamidone;

hydroxyanilide compounds, such as fenhexamid;

benzenesulfonamide compounds, such as flusulfamide;

oxime ether compounds, such as cyflufenamid;

anthraquinone compounds;

crotonic compounds;

antibiotics, such as validamycin, kasugamycin and polyoxins;

guanidine compounds, such as iminoctadine and dodine;

quinoline compounds, such as 6-tert-butyl-8-fluoro-2,3-dimethylquinolin-4-yl acetate (tebufloquin);

thiazolidine compounds, such as (Z)-2-(2-fluoro-5-(trifluoromethyl)phenylthio)-2-(3-(2-methoxyphenyl)thiazolidin-2-yliden)acetonitrile (flutianil);

and other compounds, such as pyribencarb, isoprothiolane, pyroquilon, diclomezine, quinoxyfen, propamocarb hydrochloride, chloropicrin, dazomet, metam-sodium, nicobifen, metrafenone, UBF-307, diclocymet, proquinazid, amisulbrom (another name: amibromdole), 3-(2,3,4-trimethoxy-6-methylbenzoyl)-5-chloro-2-methoxy-4-methylpyridine, 4-(2,3,4-trimethoxy-6-methylbenzoyl)-2,5-dichloro-3-trifluoromethylpyridine, pyriofenone, isofetamid, mandipropamid, fluopicolide, carpropamid, meptyldinocap, spiroxamine, S-2188 (fenpyrazamine), S-2200, ZF-9646, BCF-051, BCM-061 and BCM-062.

In the present invention, the blend ratio of the respective components cannot generally be defined, since it varies depending upon conditions such as formulation ingredients, the type of the formulation, the application site, etc. However, for example, flonicamid or its salt is used in an amount of from 1 to 50 parts by weight, preferably from 5 to 37.5 parts by weight, the organic silicone type surfactant is used in an amount of from 0.1 to 50 parts by weight, preferably from 1 to 27.5 parts by weight, and the vegetable oil is used in an amount of from 30 to 98.9 parts by weight, preferably from 35 to 94 parts by weight.

Further, in a case where an emulsifying agent is blended, its amount is from 3 to 30 parts by weight, preferably from 5 to 20 parts by weight. In a case where an anti-settling agent is blended, its amount is from 0.1 to 5 parts by weight, preferably from 0.5 to 2.5 parts by weight. In a case where an antifoaming agent is blended, its amount is from 0.01 to 5 parts by weight, preferably from 0.1 to 2 parts by weight. In a case where at least one agricultural chemical component other than flonicamid is blended, its amount is from 1 to 50 parts by weight, preferably from 5 to 40 parts by weight.

In the present invention, the blend ratio (organic silicone type surfactant: oil-based diluting agent) of the organic silicone type surfactant to the oil-based diluting agent, by weight, with which more excellent foaming-suppressing effects will be achieved, is usually from 1:94 to 1:1, preferably from 1:80 to 1:2.

The oil-based pesticidal suspension of the present invention thus prepared suppresses foaming when diluted with water at the time of its use, provides stable physical and chemical performance and in addition, has excellent pesticidal effects.

Now, some preferred embodiments of the pesticidal suspension of the present invention are mentioned below, however, the present invention is not limited thereto.

[1] An oil-based pesticidal suspension comprising (1) flonicamid or its salt, (2) an organic silicone type surfactant and (3) at least one oil-based diluting agent selected from the group consisting of a vegetable oil and its alkylated oil.

[2] The oil-based pesticidal suspension according to the above [1], wherein the organic silicone type surfactant is a compound represented by the formula (I):

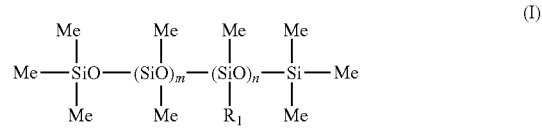

{wherein $R_1$ is an organic group represented by the following formula (II):

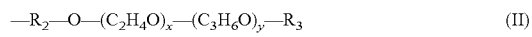

(wherein $R_2$ is a non-substituted or substituted $C_{2-6}$ alkylene group, $R_3$ is a hydroxy group, a non-substituted or substituted $C_{1-6}$ alkyl group or an acetyl group (—$COCH_3$), Me is a methyl group, x is an integer of from 0 to 15, and y is an integer of from 0 to 10), m is an integer of from 0 to 10, and n is an integer of from 1 to 10}.

[3] The oil-based pesticidal suspension according to the above [1] or [2], wherein the oil-based diluting agent is at least one oil-based diluting agent selected from the group consisting of olive oil, kapok oil, castor oil, papaya oil, camellia oil, coconut oil, sesame oil, corn oil, rice bran oil, peanut oil, cottonseed oil, soybean oil, rapeseed oil, linseed oil, tung oil, sunflower oil, safflower oil and their methylated oils.

[4] The oil-based pesticidal suspension according to the above [1] to [3], wherein the oil-based diluting agent is at least one oil-based diluting agent selected from the group consisting of olive oil, corn oil, soybean oil, rapeseed oil and their methylated oils.

[5] The oil-based pesticidal suspension according to the above [1] to [4], wherein the oil-based diluting agent is at least one oil-based diluting agent selected from the group consisting of methylated soybean oil and methylated rapeseed oil.

[6] The oil-based pesticidal suspension according to the above [1] to [5], wherein the oil-based diluting agent is methylated rapeseed oil.

[7] The oil-based pesticidal suspension according to the above [1] to [6], which further contains an emulsifying agent.

[8] The oil-based pesticidal suspension according to the above [1] to [7], wherein the emulsifying agent is at least one emulsifying agent selected from the group consisting of an alkane sulfonate, a salt of α-sulfofatty acid, a dialkyl sulfosuccinate, an alkylaryl sulfonate, a salt of a condensate of naphthalene sulfonate with formalin, a polyoxyethylene alkyl ether, a polyoxyethylene alkylaryl ether, a polyoxyethylene styryiphenyl ether, a polyoxyethylene fatty acid ester, a polyoxyethylene sorbitan fatty acid ester, a polyoxyethylene sorbitol fatty acid ester, a polyoxyethylene castor oil, a polyoxyethylene hydrogenated castor oil, a polyglycerin fatty acid ester and a polyoxyethylene polyoxypropylene block copolymer.

[9] The oil-based pesticidal suspension according to the above [1] to [8], wherein the emulsifying agent is at least one emulsifying agent selected from the group consisting of a dialkyl sulfosuccinate, an alkylaryl sulfonate, a polyoxyethylene fatty acid ester, a polyoxyethylene sorbitol fatty acid ester, a polyoxyethylene castor oil and a polyoxyethylene hydrogenated castor oil.

[10] The oil-based pesticidal suspension according to the above [1] to [9], wherein the emulsifying agent is at least one emulsifying agent selected from the group consisting of an alkylaryl sulfonate, a polyoxyethylene sorbitol fatty acid ester and a polyoxyethylene castor oil.

[11] The oil-based pesticidal suspension according to the above [1] to [10], wherein the blend ratio, by weight, of the organic silicone type surfactant to the oil-based diluting agent is from 1:94 to 1:1.

[12] The oil-based pesticidal suspension according to the above [1] to [10], wherein the blend ratio, by weight, of the organic silicone type surfactant to the oil-based diluting agent is from 1:80 to 1:2.

[13] A method for controlling pests, which comprises applying a pesticidally effective amount of the oil-based pesticidal suspension as defined in the above [1] to [12] to the pests or to a place where they grow.

[14] A method of suppressing foaming which occurs when an oil-based pesticidal suspension comprising (1) flonicamid or its salt, (2) an organic silicone type surfactant and (3) at least one oil-based diluting agent selected from the group consisting of a vegetable oil and its alkylated oil, is diluted with water, by the oil-based diluting agent (3).

[15] The method according to the above [14], wherein the oil-based pesticidal suspension is the oil-based pesticidal suspension as defined in the above [2] to [12].

[16] Use of (3) at least one oil-based diluting agent selected from the group consisting of a vegetable oil and its alkylated oil, to suppress foaming which occurs when an oil-based pesticidal suspension comprising (1) flonicamid or its salt, (2) an organic silicone type surfactant and the oil-based diluting agent (3), is diluted with water.

[17] Use of an oil-based diluting agent according to [16], to suppress foaming which occurs when the oil-based pesticidal suspension as defined in the above [2] to [12] is diluted with water.

EXAMPLES

Now, the present invention will be described in further detail, but it should be understood that the present invention is by no means restricted thereto.

First, Formulation Examples of the present invention will be described.

Formulation Example 1

(a) Flonicamid (97%) . . . 10.5 parts by weight
(b) A mixture containing polyoxyethylene sorbitol fatty acid ester (tradename: Sorpol 4300, manufactured by TOHO Chemical Industry Co., Ltd.) . . . 12.0 parts by weight
(c) Organic bentonite (tradename: New D ORBEN, manufactured by Shiraishi Kogyo Kaisha, Ltd.) . . . 1.0 part by weight
(d) Methylated rapeseed oil (tradename: Agnique ME 18RD-F, manufactured by BASF) . . . 59.8 parts by weight
(e) Polyoxyalkylene methyl polysiloxane (tradename: KF-640, manufactured by Shin-Etsu Chemical Co., Ltd.) . . . 16.7 parts by weight The above (a) to (d) were mixed and stirred, and the resulting solution was wet-ground by DYNO-MILL to obtain a ground slurry, to which the above (e) was added to obtain an oil-based pesticidal suspension.

Formulation Example 2

(a) Flonicamid (97%) . . . 10.5 parts by weight
(b) Oleate of polyoxyethylene castor oil (tradename: Alkamuls VO/2003, manufactured by Rhodia Nicca) . . . 12.0 parts by weight
(c) Synthetic silica (tradename: AEROSIL R974, manufactured by Nippon Aerosil Co., Ltd.) . . . 1.0 part by weight
(d) Methylated rapeseed oil (tradename: Agnique ME 18RD-F, manufactured by BASF) . . . 59.8 parts by weight
(e) Trisiloxane ethoxylate (tradename: Silwet L-77, manufactured by Momentive Performance Materials Inc.) . . . 16.7 parts by weight The above (a) to (d) were mixed and stirred, and the resulting solution was wet-ground by DYNO-MILL to obtain a ground slurry, to which the above (e) was added to obtain an oil-based pesticidal suspension.

Formulation Example 3

(a) Flonicamid (97%) . . . 10.5 parts by weight
(b) Oleate of polyoxyethylene castor oil (tradename: Alkamuls VO/2003, manufactured by Rhodia Nicca) . . . 20.0 parts by weight
(c) Organic bentonite (tradename: New D ORBEN, manufactured by Shiraishi Kogyo Kaisha, Ltd.) . . . 1.0 part by weight
(d) Methylated rapeseed oil (tradename: Agnique ME 18RD-F, manufactured by BASF) . . . 51.8 parts by weight
(e) Polyoxyalkylene methyl polysiloxane (tradename: KF-640, manufactured by Shin-Etsu Chemical Co., Ltd.) . . . 16.7 parts by weight The above (a) to (d) were mixed and stirred, and the resulting solution was wet-ground by DYNO-MILL to obtain a ground slurry, to which the above (e) was added to obtain an oil-based pesticidal suspension.

Formulation Example 4

(a) Flonicamid (97%) . . . 10.5 parts by weight
(b) A mixture containing polyoxyethylene hydrogenated castor oil (tradename: Sorpol 3815A, manufactured by TOHO Chemical Industry Co., Ltd.) . . . 12.0 parts by weight
(c) Organic bentonite (tradename: New D ORBEN, manufactured by Shiraishi Kogyo Kaisha, Ltd.) . . . 1.0 part by weight
(d) Corn oil (manufactured by Ajinomoto Co., Inc.) . . . 63.2 parts by weight
(e) Trisiloxane ethoxylate (tradename: Silwet L-77, manufactured by Momentive Performance Materials Inc.) . . . 13.3 parts by weight The above (a) to (d) were mixed and stirred, and the resulting solution was wet-ground by DYNO-MILL to obtain a ground slurry, to which the above (e) was added to obtain an oil-based pesticidal suspension.

Formulation Example 5

(a) Flonicamid (97%) . . . 10.5 parts by weight
(b) A mixture containing polyoxyethylene hydrogenated castor oil (tradename: Sorpol 3815A, manufactured by TOHO Chemical Industry Co., Ltd.) . . . 12.0 parts by weight
(c) Organic bentonite (tradename: New D ORBEN, manufactured by Shiraishi Kogyo Kaisha, Ltd.) . . . 1.0 part by weight
(d) Methylated rapeseed oil (tradename: Agnique ME 18RD-F, manufactured by BASF) . . . 59.1 parts by weight
(e) Trisiloxane ethoxylate (tradename: Silwet L-77, manufactured by Momentive Performance Materials Inc.) . . . 16.7 parts by weight
(f) Polydimethylsiloxane (tradename: SAG1529, manufactured by Momentive Performance Materials Inc.) . . . 0.7 part by weight The above (a) to (d) were mixed and stirred, and the resulting solution was wet-ground by DYNO-MILL to obtain a ground slurry, to which the above (e) and (f) were added to obtain an oil-based pesticidal suspension.

Comparative Example 1

(a) Flonicamid (97%) . . . 10.5 parts by weight
(b) Polyoxyalkylene-methyl polysiloxane (tradename: KF-640, manufactured by Shin-Etsu Chemical Co., Ltd.) . . . 16.7 parts by weight
(c) N,N-dimethylacetamide . . . 72.8 parts by weight The above (a) and (b) were dissolved in the above (c) to obtain a 10% solution.

Now, Test Examples of the present invention will be described.

Test Example 1

Foamability Test 1

200 mL of CIPAC standard water D was put into a 250 mL graduated cylinder with a stopper, and 0.4 g (corresponding to a composition diluted 500-fold) or 1.0 g (corresponding to a composition diluted 200-fold) of the oil-based pesticidal suspension prepared in Formulation Example 1 or the solvent prepared in Comparative Example 1, which is a formulation containing an organic silicone type surfactant, was added, and the stopper was put on the cylinder. The cylinder was inverted 30 times and left at rest. One minute and three minutes later, the volume of foam was measured. Here, "inverted" means that an operation of rotating the cylinder 180° and returning it to original position was carried out in about 2 seconds. The results are shown in Table 1.

TABLE 1

| | Volume (mL) of foam | | | |
| | Diluted 200-fold | | Diluted 500-fold | |
| | After one minute | After 3 minutes | After one minute | After 3 minutes |
| Formulation Example 1 | 24 | 20 | 18 | 18 |

TABLE 1-continued

| | Volume (mL) of foam | | | |
| | Diluted 200-fold | | Diluted 500-fold | |
| | After one minute | After 3 minutes | After one minute | After 3 minutes |
| Comparative Example 1 | 108 | 108 | 90 | 87 |

Test Example 2

Biological Effect Test

The numbers of apterous adults and nymphs of green peach aphid parasitized on a 5- to 7-foliate radish planted in a pot having a diameter of 15 cm, were counted. The oil-based pesticidal suspension prepared in Formulation Example 1 diluted with water to an active ingredient concentration of 60 ppm was applied to the radish for foliage treatment by spraying in a water amount corresponding to 500 liters/ha. Immediately after the treatment, the pot was kept in an outdoor biotron (10° C.). 5, 10 and 14 days after the application, the numbers of parasitic green peach aphid were counted in the same manner as above, and the controlling value (%) was calculated by the following formula. The results are shown in Table 2.

Controlling value=$(1-(Tan \times Cb)/(Tb \times Can)) \times 100$ $Cb$=The number of green peach aphid in non-treated section before treatment
$Tb$=The number of green peach aphid in treated section before treatment
$Can$=The number of green peach aphid in non-treated section n-days after treatment
$Tan$=The number of green peach aphid in treated section n-days after treatment

TABLE 2

| | Controlling value (%) | | |
| | After 5 days | After 10 days | After 14 days |
| Formulation Example 1 | 78.4 | 96.3 | 97.6 |

As evident from the results in Test Example 1 and Test Example 2, the oil-based pesticidal suspension of the present invention remarkably suppresses foaming at the time of preparation of a spray solution by addition of an organic silicone type surfactant, provides stable physical and chemical performance and in addition, has excellent pesticidal effects. Thus, it is an oil-based pesticidal suspension which can realize reduction of the dose of the agricultural chemical.

Test Example 3

Foamability Test 2

The foamability test was carried out with respect to the oil-based pesticidal suspensions of the present invention having the respective compositions as identified in the following Table 3. The test was carried out in the same manner as in Text Example 1 with respect to each composition diluted 500-fold. The results are shown in Table 3.

TABLE 3

| Component (parts by weight) | | | | | | | | |
|---|---|---|---|---|---|---|---|---|
| Flonicamid | | 10.54 | | | | | | |
| Sorpol 4300 | | 8.00 | | | | | | |
| Silwet L-77 | | 35.00 | 30.00 | 27.50 | 25.00 | 20.00 | 10.00 | 1.00 |
| Agnique ME 18RD-F | | 46.46 | 51.46 | 53.96 | 56.46 | 61.46 | 71.46 | 80.46 |
| Volume (mL) of foam after one minute | | 65 | 62 | 60 | 51 | 45 | 42 | 18 |

The entire disclosure of Japanese Patent Application No. 2012-267685 filed on Dec. 6, 2012 including specification, claims and summary is incorporated herein by reference in its entirety.

The invention claimed is:

1. An oil-based pesticidal suspension comprising (1) flonicamid or its salt, (2) an organic silicone type surfactant, and (3) an oil-based diluting agent which is an alkylated vegetable oil, and (4) an emulsifying agent which is a polyoxyethylene sorbitol fatty acid ester.

2. The oil-based pesticidal suspension according to claim 1, wherein organic silicone type surfactant is a compound represented by the formula (I):

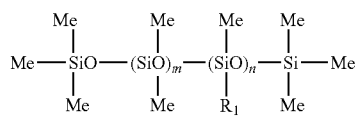

wherein $R_1$ is an organic group represented by the following formula (II):

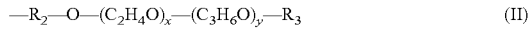

wherein $R_2$ is a non-substituted or substituted $C_{2-6}$ alkylene group, $R_3$ is a hydroxy group, a non-substituted or substituted $C_{1-6}$ alkyl group or an acetyl group ($-COCH_3$), Me is a methyl group, x is an integer of from 0 to 15, and y is an integer of from 0 to 10, m is an integer of from 0 to 10, and n is an integer of from 1 to 10.

3. The oil-based pesticidal suspension according to claim 1, wherein the oil-based diluting agent is at least one oil-based diluting agent selected from the group consisting of methylated olive oil, methylated kapok oil, methylated castor oil, methylated papaya oil, methylated camellia oil, methylated coconut oil, methylated sesame oil, methylated corn oil, methylated rice bran oil, methylated peanut oil, methylated cottonseed oil, methylated soybean oil, methylated rapeseed oil, methylated linseed oil, methylated tung oil, methylated sunflower oil and methylated safflower.

4. The oil-based pesticidal suspension according to claim 1, wherein the oil-based diluting agent is at least one oil-based diluting agent selected from the group consisting of methylated olive oil, methylated corn oil, methylated soybean oil and methylated rapeseed oil.

5. The oil-based pesticidal suspension according to claim 1, wherein the oil-based diluting agent is at least one oil-based diluting agent selected from the group consisting of methylated soybean oil and methylated rapeseed oil.

6. A method for controlling pests, which comprises applying a pesticidally effective amount of the oil-based pesticidal suspension as defined in claim 1 to the pests or to a place where they grow.

7. A method of suppressing foaming which occurs when an oil-based pesticidal suspension comprising (1) flonicamid or its salt, (2) an organic silicone type surfactant and (3) an oil-based diluting agent which is an alkylated vegetable oil, and (4) an emulsifying agent which is a polyoxyethylene sorbitol fatty acid ester, is diluted with water, by the oil-based diluting agent (3), wherein the method comprises (i) diluting the suspension with water and (ii) suppressing foaming by the oil-based diluting agent (3) and an emulsifying agent (4).

8. A method of suppressing foaming which occurs when diluting (1) flonicamid or its salt and (2) an organic silicone type surfactant with water, comprising conducting the diluting in the presence of an oil-based diluting agent (3) which is an alkylated vegetable oil and (4) an emulsifying agent which is a polyoxyethylene sorbitol fatty acid ester.

9. The method according to claim 8, wherein a blend ratio, by weight, of the organic silicone type surfactant to the oil-based diluting agent is from 1:94 to 1:1.

10. The method according to claim 8, wherein a blend ratio, by weight, of the organic silicone type surfactant to the oil-based diluting agent is from 1:80 to 1:2.

11. The oil-based pesticidal suspension according to claim 1, wherein a blend ratio, by weight, of the organic silicone type surfactant to the oil-based diluting agent is from 1:94 to 1:1.

12. The oil-based pesticidal suspension according to claim 1, wherein a blend ratio, by weight, of the organic silicone type surfactant to the oil-based diluting agent is from 1:80 to 1:2.

* * * * *